US00PP23177P2

(12) United States Plant Patent
Durand

(10) Patent No.: US PP23,177 P2
(45) Date of Patent: Nov. 13, 2012

(54) ***PHYSOCARPUS* PLANT NAMED 'JEFAM'**

(50) Latin Name: *Physocarpus opulifolius*
Varietal Denomination: 'Jefam'

(75) Inventor: James Richard Durand, Portage la Prairie (CA)

(73) Assignee: Jeffries Nurseries, Manitoba, Portage la Prairie (CA)

( * ) Notice: Subject to any disclaimer, the term of this patent is extended or adjusted under 35 U.S.C. 154(b) by 78 days.

(21) Appl. No.: 12/928,656

(22) Filed: Dec. 16, 2010

(51) Int. Cl.
*A01H 5/00* (2006.01)

(52) U.S. Cl. ..... Plt./226

(58) Field of Classification Search ..... Plt./226
See application file for complete search history.

(56) References Cited

OTHER PUBLICATIONS

Growing Matters. Jul. 2010, vol. 13: Issue 2, 3 pp.*
Pluto Plant Variety Database 2011/06 retrieved on Apr. 12, 2012. Retrieved from the Internet at <http://www.upov.int/pluto/en/> one page.*

* cited by examiner

*Primary Examiner* — June Hwu
(74) *Attorney, Agent, or Firm* — Penny J. Aguirre

(57) ABSTRACT

A new cultivar of *Physocarpus*, 'Jefam', that is characterized by its unique foliage coloration with leaves that emerges bright orange in spring, turn green on older wood, and become purple in fall, its oblate plant shape and its compact plant habit.

2 Drawing Sheets

Genus/species: *Physocarpus opulifolius.*
Varietal denomination: 'Jefam'.

BACKGROUND OF THE INVENTION

The present invention relates to a new and distinct cultivar of *Physocarpus opulifolius* and will be referred to hereafter by its cultivar name, 'Jefam'. 'Jefam' represents a new cultivar of *Physocarpus*, a deciduous shrub grown for landscape use.

The new *Physocarpus* arose from a breeding program conducted by the Inventor at a nursery in Portage la Prairie, Manitoba, Canada. The objective of the breeding program was to develop new *Physocarpus* cultivars with unique foliage color combined with compact plant habits.

The new *Physocarpus* originated from a cross-pollination made by the Inventor in spring of 2003. The female parent was *Physocarpus opulifolius* 'Monlo' (U.S. Plant Pat. No. 11,211) and the male parent was *Physocarpus opulifolius* 'Dart's Gold' (not patented). 'Jefam' was selected as a unique single plant from the progeny resulting from the cross-pollination in spring of 2006.

Asexual reproduction of the new cultivar was first accomplished by softwood cuttings in Portage la Prairie, Manitoba, Canada by the Inventor. The characteristics of this cultivar have been determined to be stable and are reproduced true to type in successive generations.

SUMMARY OF THE INVENTION

The following traits have been repeatedly observed and represent the characteristics of the new *Physocarpus*. These attributes in combination distinguish 'Jefam' as unique and distinct from all other cultivars of *Physocarpus* known to the Inventor.

1. The new foliage of 'Jefam' emerges bright orange in color in spring.

2. The foliage of 'Jefam' is green in color on older wood and new growth in summer.
3. The new foliage of 'Jefam' is purple in color in fall.
4. The plant habit of 'Jefam' is oblate in shape and compact.

'Jefam' is most closely compared to its parent plants. 'Monlo', the female parent, differs from 'Jefam' in having foliage that is green in color in spring and purple in color on older wood. 'Dart's Gold', the male parent, differs from 'Jefam' in having foliage that is yellow to gold in color in spring and bronze in color in fall. 'Jefam' can also be compared to 'Center Glow' (U.S. Plant Pat. No. 16,894). 'Center Glow' differs from 'Jefam' in having foliage that emerges bright red with a gold region near the leaf base in spring and gradually changing to purple-red in summer and fall.

BRIEF DESCRIPTION OF THE DRAWING

The accompanying photographs were taken of a three year-old plant of 'Jefam' as grown outdoors in a trial bed Portage la Prairie, Manitoba, Canada and are representative of the of the new *Physocarpus*.

The photograph in FIG. 1 was taken in spring and provides a view of the plant habit of 'Jefam'.

Figure 1:
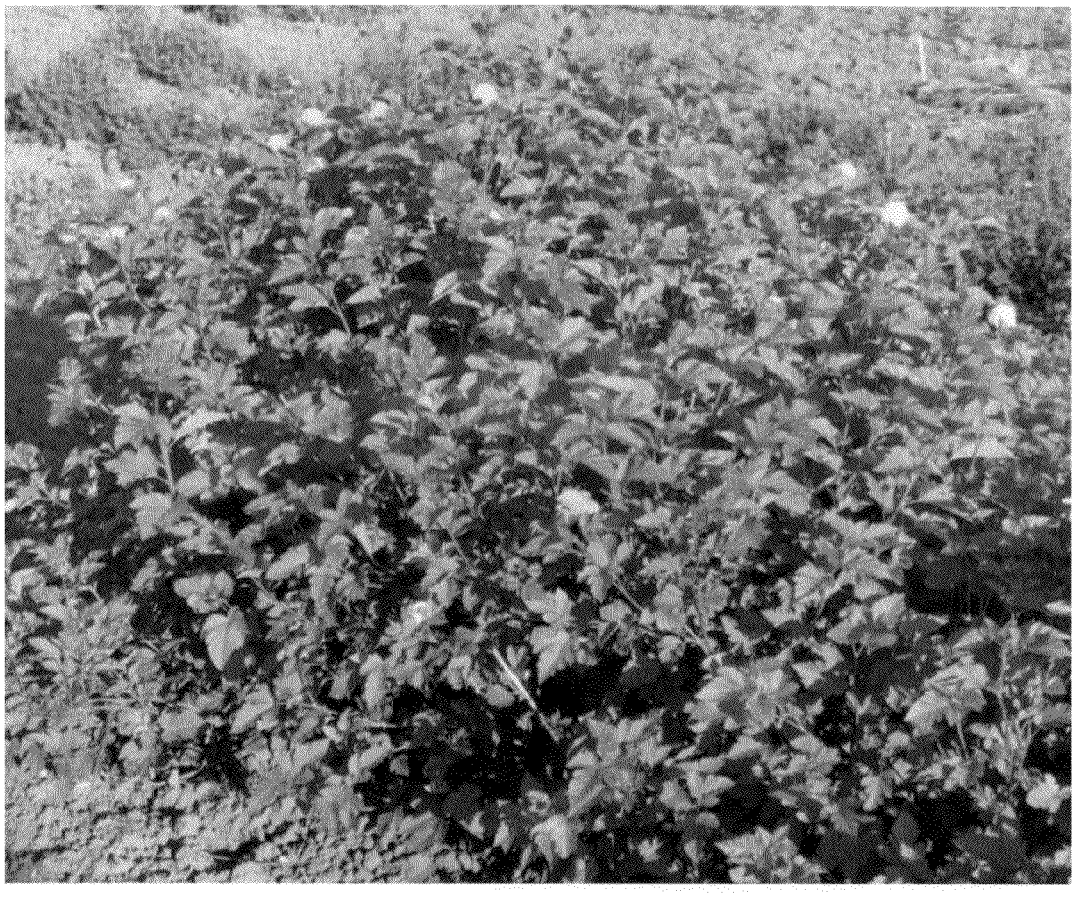
Figure 2:
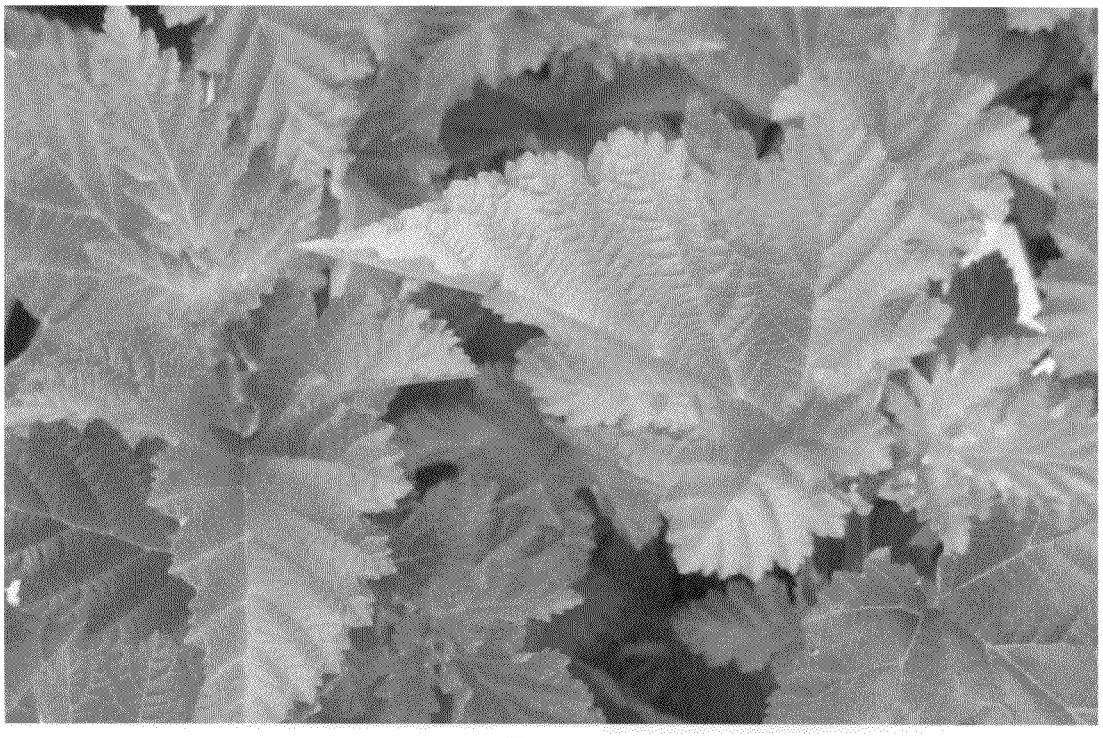

The photograph in FIG. 2 provides a close-up view of the spring foliage of 'Jefam'.

Figure 3:
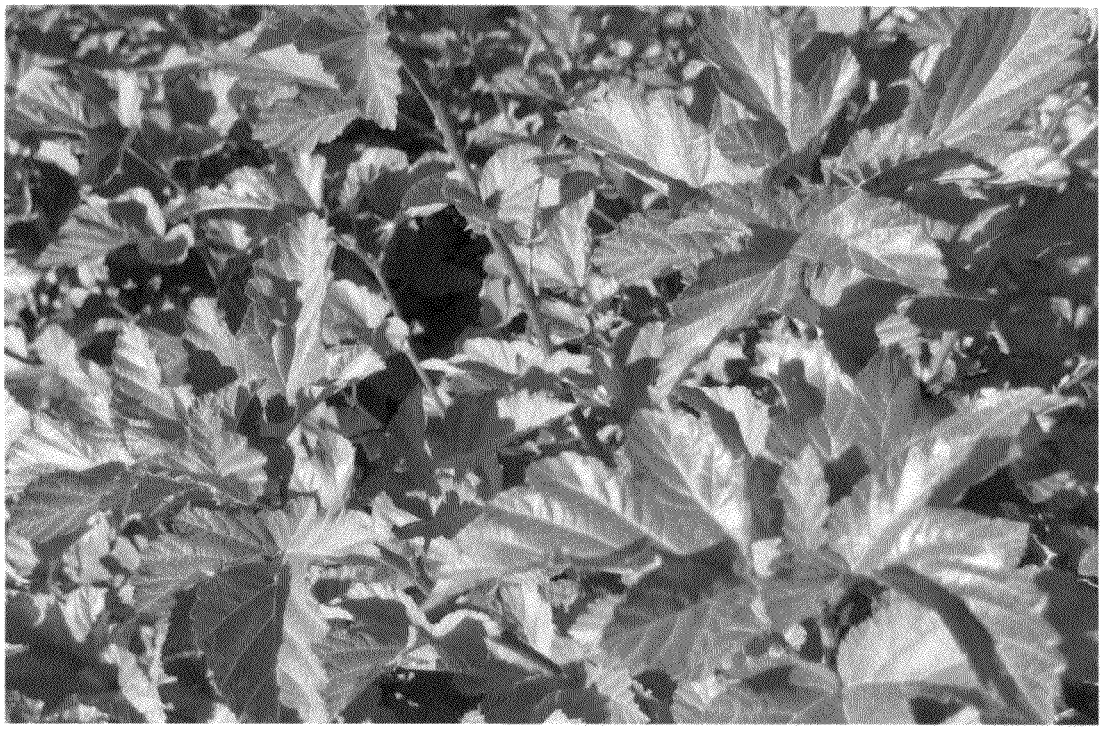

The photograph in FIG. 3 provides a close-up view of the fall foliage of 'Jefam'.

The colors in the photographs are as close as possible with the digital photography and printing techniques utilized and the color codes in the detailed botanical description more accurately describe the colors of the new *Physocarpus*.

BOTANICAL DESCRIPTION OF THE PLANT

The following is a detailed description of two year-old plants of the new cultivar as grown outdoors in 2-gallon containers in Portage la Prairie, Manitoba, Canada. Phenotypic differences may be observed with variations in environmental, climatic, and cultural conditions. The color determination is in accordance with The 2001 R.H.S. Colour Chart of the Royal Horticultural Society, London, England, except where general color terms of ordinary dictionary significance are used.

General description:

*Plant habit*.—Deciduous shrub.

*Plant habit*.—Densely foliated, oblate in shape and compact.

*Blooming period*.—2 weeks in mid summer.

*Height and spread*.—An average of 36.9 cm in height and 40.7 cm in spread.

*Hardiness*.—At least in U.S.D.A. Zone 3.

*Diseases and pest resistance*.—Good disease resistance has been observed, no susceptibility or resistance to pests has been observed.

*Growth rate*.—Vigorous.

Branch description:

*Stem color*.—New growth 144B with slight tinge of 166B, old growth twigs;166A with lenticels 187A, mature bark a blend of 165a and 165C.

*Stem shape*.—Rounded.

*Stem size*.—An average of ⅜ inch in diameter and 12 inches in height.

*Stem surface*.—New growth; glabrous with growth tips slightly pubescent, old growth twigs; glabrous, mature bark; finely barked and slightly peeling.

*Branching*.—Medium branched; an average of 9 lateral branches, medium strength.

Foliage description:

*Leaf shape*.—Ovate with oblong lobes.

*Leaf division*.—Simple.

*Leaf base*.—Cordate.

*Leaf apex*.—Acute.

*Leaf venation*.—Palmate, color new foliage in spring; upper leaf surface; 14B (distinct), lower surface 146C, color mature foliage in spring upper and lower leaf surface; 144B, color of summer foliage upper surface; 137B, color summer foliage lower surface; 146C, color fall foliage new growth and mature growth upper and lower surface; 195B.

*Leaf margin*.—3-lobed with lobes crenate.

*Leaf attachment*.—Petiolate.

*Leaf arrangement*.—Alternate.

*Leaf surface*.—Flat.

*Leaf length*.—An average of 7.22 cm.

*Leaf width*.—An average of 6.31 cm.

*Leaf number*.—About 9 per lateral branch.

*Internode length*.—An average of 7 cm.

*Leaf color*.—Spring foliage: new growth upper lower surface; a blend of 169B and 172B, new growth lower surface 144B with a tinge of 169B, mature foliage upper and lower surface; 144A to 144B, summer foliage: new growth and mature foliage; upper surface 137B, lower surface 138B, fall foliage: new growth upper surface; 174A, new growth lower surface and mature growth upper and lower surface; 138B with slight tinge of 174A.

*Petiole size*.—About ⅞ inch in length, about ⅛ inches in width.

*Petiole shape*.—Sulcate.

*Petiole color*.—166A.

*Petiole texture*.—Glabrous, no gloss.

*Stipules*.—None.

Flower description:

*Flower type*.—Small rotate flowers arranged in spherical corymb, similar to parents and typical of the species *Physocarpus opulifolius*.

*Flower fragrance*.—Slight.

*Flower lastingness*.—Corymb lasts about 2 weeks, not persistent, individual flowers about 3 days.

*Flower bud description*.—Elliptic in shape, average of 3.3 cm in length and 3 mm in diameter, 65D in color.

*Flower quantity*.—About 50 flowers per corymb.

*Inflorescence size*.—About 3 cm in depth and diameter.

*Flower size*.—About 6 mm in depth, 8 mm in diameter.

*Peduncles*.—About 1.4 cm in length and 2 mm in diameter, 144A in color, glabrous surface.

*Pedicels*.—About 1.8 cm in length and 1 mm in diameter, 144A in color, glabrous surface.

*Petal description*.—5, elliptic to obovate in shape, margin is entire, apex is broadly acute, lower and upper surface is glabrous, apex is obtuse, base is attenuate.

*Petal size*.—About 4.5 mm in length and width.

*Petal color*.—Opening; upper surface 158D, lower 158D with tinge of 65C, Fully open; upper and lower surface 155D turning slightly greyer as they age.

*Calyx size*.—Average of 8 mm in length and diameter.

*Sepal description*.—5, subulate in shape, margin is entire, apex is acute, surface is glabrous, an average of 1.7 cm in length and 2.8 mm in width, color is 144A when developing, turning to 75B after anthesis.

Reproductive organs:

*Gynoecium*.—4, Pistil about 0.5 mm in length, stigma is globular in shape and 145B in color, style is about 0.4 mm in length and 145B in color, ovary is 145B in color.

*Androecium*.—An average of 25, anthers are oblong in shape, about 0.5 mm in length and 46A in color, pollen is scarce in abundant and 46A in color.

*Fruit and seed*.—Fruit a firm-walled inflated follicle, splitting open at both seams, ovoid in shape, seeds; 2 to 4 seeds are hard, shiny, ovoid in shape, N199 in color at maturity.

It is claimed:

1. A new and distinct cultivar of *Physocarpus* plant named 'Jefam' substantially as herein illustrated and described.

* * * * *